United States Patent
Norddahl

(10) Patent No.: US 6,319,382 B1
(45) Date of Patent: Nov. 20, 2001

(54) FERMENTATIVE PRODUCTION AND ISOLATION OF LACTIC ACID

(75) Inventor: Birgir Norddahl, Ringe (DK)

(73) Assignee: Lactascan ApS, Odense (DK)

( * ) Notice: Subject to any disclaimer, the term of this patent is extended or adjusted under 35 U.S.C. 154(b) by 0 days.

(21) Appl. No.: 09/331,665

(22) PCT Filed: Dec. 22, 1997

(86) PCT No.: PCT/DK97/00596

§ 371 Date: Aug. 11, 1999

§ 102(e) Date: Aug. 11, 1999

(87) PCT Pub. No.: WO98/28433

PCT Pub. Date: Jul. 2, 1998

(30) Foreign Application Priority Data

Dec. 23, 1996 (DK) .................................................... 1496/96

(51) Int. Cl.⁷ .................................................... B01D 61/44
(52) U.S. Cl. ..................... 204/530; 204/531; 204/534; 204/537; 204/538
(58) Field of Search ..................... 204/530, 531, 204/534, 537, 538

(56) References Cited

U.S. PATENT DOCUMENTS

| | | |
|---|---|---|
| 4,110,175 | 8/1978 | Ahlgren et al. . |
| 4,698,303 | 10/1987 | Bailey et al. . |
| 5,002,881 | 3/1991 | Van Nispen et al. . |
| 5,464,760 * | 11/1995 | Tsai et al. . |
| 5,503,750 * | 4/1996 | Russo, Jr. et al. ................... 210/641 |
| 5,681,728 * | 10/1997 | Miao ................................... 204/530 |

FOREIGN PATENT DOCUMENTS

| | | |
|---|---|---|
| 230021B1 | 7/1987 | (EP) . |
| 0393818 | 10/1990 | (EP) . |
| 9641021 | 12/1996 | (WO) . |

OTHER PUBLICATIONS

Boyaval et al., Biotecnology Letters, vol. 9, No. 3, 207–212, 1987.
Boyaval et al., Appl. Microbiol. Biotechnol. 30:528–534, 1989.
Boyaval et al., Le Lait, 68(1):65–84, 1988 (in French with English Abstract).

* cited by examiner

Primary Examiner—Arun S. Phasge
(74) Attorney, Agent, or Firm—Birch, Stewart, Kolasch & Birch, LLP

(57) ABSTRACT

A method for fermentation of lactic acid from a sugar-containing fermentation liquid in a fermentor by means of lactic acid-forming bacteria, in which whey protein is present or is added as a nutrient substrate for the lactic acid-forming bacteria, wherein at least one protease is added to the fermentor during the fermentation, so that hydrolysis of protein to amino acids takes place simultaneously with the fermentation of sugar into organic acid, and wherein lactic acid resulting from the fermentation is isolated from the fermentation liquid. Ammonia is preferably added to result in the formation of ammonium lactate, and lactic acid is preferably isolated by a process comprising ultra filtration, ion exchange, conventional electrodialysis and electrodialysis with bipolar membranes.

11 Claims, No Drawings

FERMENTATIVE PRODUCTION AND ISOLATION OF LACTIC ACID

This application is the national phase under 35 U.S.C. §371 of PCT International Application No. PCT/DK97/00596 which has an International filing date of Dec. 22, 1997 which designated the United States of America.

FIELD OF THE INVENTION

The present invention relates a process for the fermentative production of lactic acid and for the isolation of lactic acid from a lactic acid-containing solution.

BACKGROUND OF THE INVENTION

European patent No. 230.021 describes a process in which glucose is fermented continuously to lactate, after which lactic acid is extracted from the solution by means of electrodialysis, where pH in the fermentor is controlled by removing the lactic acid at the same rate as the rate at which it is formed, the contents of the fermentor being recirculated over the electrodialysis unit. Yeast extract and inorganic salts are used as nutrients. A disadvantage of this system is that bacteria in the fermentor liquid are known to adsorb to the electrodialysis membranes, causing the electrical resistance in the electrodialysis unit to increase, which results in a substantially increased power consumption for the electrodialysis process.

Boyaval et al. (*Biotechnology Letters* Vol. 9, No. 3, 207–212, 1987) describe a bioreactor for lactic acid fermentation using a three-stage fermentation process that includes the production of biomass and lactic acid in the first stage, separation and concentration of the cells by ultrafiltration in the second stage, and lactate concentration and purification by electrodialysis in the third stage. It is reported, however, that this system exhibits the disadvantage of clogging of the ultrafiltration membranes, resulting in drastic restriction of permeate flow.

U.S. Pat. No. 4,110,175 also describes a general method for electrolytic purification of organic acids, including lactic acid. An improved version of this method is described in U.S. Pat. No. 5,002,881, in which lactic acid is formed as ammonium lactate through fermentation of a glucose-containing medium, which makes it possible to use ultrafiltration to separate the ammonium lactate from the fermentation liquid, as the retentate from the ultrafilter is returned to the fermentor. In this way there is no adsorption of bacteria to the membranes in the subsequent electrodialysis processes, and power consumption is therefore lower. The microorganism used in the patent is *Bacillus coagulans*, which has the property of not needing any special nutrient medium containing yeast extract or corn steep liquor, which are otherwise known to be necessary to maintain lactic acid fermentation when lactic acid bacteria are used. Prior to electrodialysis, the fermentor liquid is concentrated by means of reverse osmosis (RO), and the concentrated liquid is subsequently treated in an electrodialysis unit in which lactic acid is formed from ammonium lactate by means of bipolar membranes in a single operation. In this operation ammonium hydroxide is formed at the same time and can be returned to the fermenter as a medium for neutralisation of lactic acid. in this process, however, amino acids are used as a nutrient for the fermenting bacteria, which results in the disadvantage of relatively high costs. A further disadvantage is that RO used for concentration will result in non-converted organic matter (residual glucose and amino acids) being included in the electrodialysis treatment with bipolar membranes, where they contribute to reducing the process efficiency. Also, the resulting product might not be heat-stable due to the presence of residual sugars in the lactic acid.

The formation of amino acids from whey proteins and the use of whey protein as a nutrient in the fermentation of lactose in whey is described in U.S. Pat. No. 4,698,303. However, U.S. Pat. No. 4,698,303 has the disadvantage of requiring an independent hydrolysis for the production of amino acids from whey protein, the hydrolysis being carried out as a separate acidic enzymatic process, after which the hydrolysed product is fed to the membrane fermenter as a nutrient.

U.S. Pat. No. 5,503,750 discloses a method for the production and recovery of lactic acid using a combination of ultrafiltration (UF), nanofiltration (NF) and reverse osmosis (RO).

WO 96/41021 discloses a method for recovering and purifying organic acids, e.g. lactic acid, using electrodialysis, where nanofiltration and contact with a chelating agent are employed to reduce fouling of ion-selective membranes used in electrodialysis.

EP 0393818-A discloses a method for purifying lactic acid using an electrodialysis step, a bipolar electrodialysis step, treatment with a strong cationic ion exchange resin and treatment with a weak anionic ion exchange resin.

BRIEF DISCLOSURE OF THE INVENTION

It is an object of the present invention to provide a process by which lactic acid can be produced and isolated in a simple and inexpensive manner, so as to eliminate the disadvantages of the prior art processes discussed above.

One aspect of the present invention thus relates to a method for fermentation of lactic acid from a sugar-containing fermentation liquid in a fermentor by means of lactic acid-forming bacteria, in which whey protein is present or is added as a nutrient substrate for the lactic acid-forming bacteria, the method comprising adding at least one protein-hydrolysing enzyme to the fermentor during the fermentation, so that hydrolysis of protein to amino acids takes place simultaneously with the fermentation of sugar into organic acid, and isolating lactic acid resulting from the fermentation.

DETAILED DESCRIPTION OF THE INVENTION

According to the invention, a sterilised growth medium comprising a sugar-containing solution and whey protein, e.g. whey permeate from production of whey protein concentrate, with an admixture of protein-hydrolysing enzymes, in the following called proteases, is subjected to continuous fermentation in a fermentor by means of a bacteria culture which produces lactic acid.

The "sugar" in the sugar-containing solution used according to the present invention can be any suitable sugar for lactic acid fermentation, for example a monosaccharide such as glucose, fructose or galactose, a disaccharide such as sucrose, maltose, cellobiose or lactose, or a polysaccharide. A mixture of different sugars can of course also be used. The sugar may suitably be derived e.g. from a whey permeate, but it may also be derived from any other source.

In a preferred embodiment, the pH in the fermentation liquid is kept substantially constant within the range of about pH 5–7 by addition of ammonia, typically in the form of ammonia gas, which forms a water-soluble salt with lactic acid. Although it is possible to maintain the desired pH value by means of other bases, e.g. NaOH, Ca(OH)$_2$ or CaCO$_3$, this is less preferred for several reasons, among them being the fact that calcium ions are undesired in the fermentation liquid, and the fact that ammonia is less expensive than bases such as NaOH. Furthermore, the use of ammonia as the base has the advantage that it provides a source of nitrogen for the lactic acid bacteria, which has been found to result in improved growth of the bacteria compared to e.g. NaOH.

In another preferred embodiment, the fermentation liquid is subjected to an ultrafiltration process which retains the retentate containing bacteria culture and non-hydrolysed whey protein, and allows dissolved matter to pass, including lactic acid formed in the fermentation process. The lactic acid may e.g. be in the form of ammonium lactate when ammonia is added as a base as described above.

The permeate from the ultrafiltration process is then preferably treated in an ion exchange unit, preferably utilising a chelating resin which primarily binds divalent ions, so as to replace calcium and magnesium ions as well as possible iron ions present in the permeate with sodium ions, thus preventing precipitation of salts, for example calcium salts such as calcium phosphate that might otherwise lead to a slow irreversible scaling of the membranes in a subsequent electrodialysis treatment of the permeate. Moreover, the removal of iron ions results in the final lactic acid product being non-coloured.

The resulting eluate from the ion exchange operation is then preferably concentrated in an electrodialysis process, preferably a 2-step electrodialysis process in which the first step uses conventional electrodialysis membranes.

Subsequent hereto, the concentrate is preferably subjected to a second electrodialysis process in which bipolar membranes separate the salts formed into lactic acid, inorganic acids and an ammonium hydroxide solution. Ammonium lactate is hereby converted into ammonium hydroxide and lactic acid in two separate streams, a base stream and an acid stream, similar to that described in U.S. Pat. No. 5,002,881. The present invention, however, represents a simplified process, since the feed stream in the present invention contains no organic matter that can foul the bipolar electrodialysis membranes. The inorganic salts present are also split up in this step, with the positive ions in the base stream as hydroxides and the negative ions in the acid stream.

The advantage of this 2-step electrodialysis procedure is that the organic constituents such as residual sugar and amino acids that are removed in the first electrodialysis step will not later interfere with the second (bipolar) electrodialysis in which the ammonium lactate is converted into lactic acid.

The ammonium hydroxide-containing solution is typically led back to the reactor in an amount that regulates pH to the set value, e.g. a pH in the range of about 5.0–7.0, preferably about 5.5–6.5, more preferably about 5.5–6.0. The acid solution is preferably led to a strong cationic ion exchanger where cations are exchanged with hydrogen ions. The eluate from the cation exchange operation is then preferably treated in a weak anionic ion exchanger in the hydroxide form adsorbing the lactic acid. The adsorbed lactic acid is then eluted, for example using 0.5 M phosphoric acid, which only elutes the lactic acid and volatile fatty organic acids in a concentrated and very pure form, whereas other anions are retained in the anion exchange column.

As an alternative to the ion exchange procedure described above, the acid solution may be led to a third electrodialysis stage. In this case, the pH of the acid solution is adjusted with e.g. formic acid to a value of from about 1.5 to about 2.5, preferably from about 2.0 to about 2.2, to separate lactic acid from inorganic acids. Electrodialysis of this strongly acidic solution allows lactic acid to be separated from charged inorganic acids and to be collected in the diluate stream together with most of the formic acid and small amounts of acetic acid.

Although the procedure for isolation of lactic acid according to the present invention preferably comprises a combination of the above-described steps, i.e. ultrafiltration, ion exchange with a chelating resin, first electrodialysis, second electrodialysis, and cationic and anionic ion exchange or third dialysis, and preferably in the order described, it will be clear to persons skilled in the art that one or more steps in this procedure may, if desired or advantageous, be eliminated in certain cases, and/or the order of the steps may in certain cases be varied.

Finally, the lactic acid is purified and concentrated to the desired concentration, for example using a falling film multi-stage vacuum evaporator. Concentration of the lactic acid may alternatively be performed by other known methods, e.g. in a compression evaporator in which any formic acid and acetic acid are distilled off together with water.

The present invention uses whey proteins, which may be hydrolysed to amino acids by any suitable protease to provide nutrients for the fermentation. Many such proteases are commercially available, an example of which is Flavourzyme®, which is available from Novo Nordisk A/S, Denmark. As the lactic acid-forming bacteria, any suitable lactic acid-forming bacteria, or a combination of more than one lactic acid bacteria, may be used, e.g. a bacteria of the genus Lactobacillus, such as *L. heiveticus, L. delbrueckii, L. casei, L. acidophilus* or *L. bulgaricus*. The lactic acid-forming bacteria such as Lactobacillus sp. may be used alone or together with another microorganism, for example as a co-culture with e.g. *Streptococcus thermophilus*.

The use of different strains of a lactic acid bacteria such as *L. helveticus* makes it possible to form L(+), L(−) or D(−) as well as mixtures of L(+)/(−) and D(−). In the following, the term "lactic acid" is intended to refer to any one of these types of lactic acid or mixture thereof.

According to the present invention, the enzyme is added directly to the fermentor and no further arrangements are required, such as lowering of the pH, which is necessary for the process described in U.S. Pat. No. 4,698,303.

As a result of the finding by the present inventor that it is possible to add the proteolytic enzyme directly to the fermentor without any detrimental effects, fermentation and hydrolysis can take place in the same container, i.e. the fermentor, which results in a simpler and less expensive process compared to that disclosed in U.S. Pat. No. 4,698,303. Furthermore, the advantages of the process described in U.S. Pat. No. 4,698,303 are maintained when using the present invention. In particular, ultrafiltration membranes may be coupled to the fermentor without being fouled by protein, as the hydrolysis using direct addition of enzyme to the fermentor is so quick that the proteins are hydrolysed down to peptides and amino acids before any substantial protein deposits can occur.

A further advantage of using direct addition of enzymes to the fermentor is that it makes it possible to use an ultrafilter with a very small pore size, e.g. not more than about 10,000 Dalton and preferably lower. It is thus possible to maintain a constant high flux with an ultrafilter with a cut-off value of e.g. about 5000 Dalton, so that the purification of the fermentation product, the lactic acid, can be simplified, as the content of higher polymeric constituents (mainly unhydrolysed proteins, polyglucans and other polysaccharides created by the lactic acid bacteria) in the permeate from the ultrafilter coupled to the fermentor is lower than in other known systems. Finally, the use of ultrafiltration in connection with the fermentation means that the added enzymes will stay in the fermentor, as they are unable to pass through the membrane, so that the duration of action of the enzymes is longer, which makes it possible to obtain substantial savings on the consumption of enzymes as compared to other lactic acid fermentation systems.

The invention will be further illustrated in the following non-limiting example.

EXAMPLE

Lactic acid fermentation was carried out in a 100 l membrane reactor, using a Koch S4-HFK-131 spiral-wound membrane. The cut-off value of the ultrafiltration membrane was 5 kD, and the total membrane area was 7.3 m². Inlet and outlet pressures on the membrane were 4—4 and 2.9 bar, respectively.

90 l of an aqueous growth medium was made up on the basis of sweet whey, whey protein concentrate and additional nutrients, the composition of the medium being as follows:

| | |
|---|---|
| 9.5 % by weight of whey protein | |
| 4.0 % by weight of lactose | |
| 1.5 % by weight of yeast extract | |
| 0.3 % by weight of $K_2HPO_4$ | |
| 0.04 % by weight of $MgSO_4$, 7 $H_2O$ | |
| 0.015 % by weight of $MnSO_4$, 4 $H_2O$ | |
| 0.1 % by weight of Tween ® 80 | |
| 0.006 % by weight of cystein hydrochloride | |

The medium was heated to 70° C. for 45 min and cooled to the fermentation temperature of 45° C. 18 g of freeze-dried *Lactobacillus helveticus* culture and 53 g of Flavourzyme® enzyme were added. Fermentation was carried out batchwise under anaerobic conditions for 9 hours. The continuous fermentation was then started. The aqueous feed medium was based on whey permeate and had the following composition:

| | |
|---|---|
| 0.35 % by weight of whey protein | |
| 0.01 % by weight of Flavourzyme ® | |
| 4.0 % by weight of lactose | |

The pH in the reactor was adjusted to 5.75 with ammonia gas.

The biomass concentration was kept at approx. 7–8% via a continuous bleed of reactor content. With this biomass concentration, the permeate flux on the ultrafilter was constant during the fermentation and approx. 1 l/min (8.2 l/($M^2$*h)). No cleaning-in-place was done on the ultrafilter during 34 days of continuous fermentation.

The dilution rate (D) in the fermentor was varied between 0.15 and 0.3 $h^{-1}$. This had no effect on the conversion yield, which was constant at 99.5% or more during the 34 days of fermentation. The lactate concentration in the ultrafiltration permeate was 4.0%, and the productivity at D=0.3 $h^{-1}$ was 12 g/(l*h).

Further isolation of lactic acid after ultrafiltration was performed as described above, i.e. using a combination of ion exchange with a chelating resin, first electrodialysis, second electrodialysis, and cationic and anionic ion exchange. The overall recovery rate of lactic acid was quite high, about 85–90% based on the amount of sugar added to the fermentor.

What is claimed is:

1. A method for production of lactic acid from a sugar-containing fermentation liquid in a fermentor by means of lactic acid-forming bacteria, in which whey protein is present or is added as a nutrient substrate for the lactic acid-forming bacteria, the method comprising adding at least one protein-hydrolysing enzyme to the fermentor during fermentation, so that hydrolysis of protein to amino acids takes place simultaneously with the fermentation of sugar into organic acid, and isolating lactic acid resulting from the fermentation using an ultrafiltration step and subsequently at least two electrodialysis steps.

2. A method according to claim 1, wherein the pH of the fermentation liquid is maintained at a substantially constant level by addition to the fermentation liquid of ammonia, whereby ammonium lactate is formed in the fermentation liquid.

3. A method according to claim 1, wherein ultrafiltration is performed using a filter with a cut-off value that prevents passage through said filter of the protein-hydrolysing enzyme and non-hydrolysed protein.

4. A method according to claim 3, wherein the filter has a cut-off value of not more than about 10,000 Dalton.

5. A method according to claim 4, wherein the filter has a cut-off value of not more than about 5000 Dalton.

6. A method according to claim 1, wherein isolation of lactic acid further comprises, subsequent to ultrafiltration, an ion exchange step to remove calcium and magnesium ions.

7. A method according to claim 6, wherein the ion exchange step utilises a chelating resin that primarily binds divalent ions.

8. A method according to claim 1, wherein the electrodialysis includes a first electrodialysis step using conventional electrodialysis membranes and a second electrodialysis step using bipolar membranes.

9. A method according to claim 1, wherein isolation of lactic acid further comprises, subsequent to the second electrodialysis step, an ion exchange step using a strong cationic ion exchanger and an ion exchange step using a weak anionic anionic ion exchanger.

10. A method according to claim 1, wherein isolation of lactic acid further comprises, subsequent to the second electrodialysis step, a third electrodialysis step, in which the pH of the lactic acid-containing solution is adjusted to a value in the range of about 1.5–2.5.

11. A method according to claim 1, wherein the fermentation liquid contains ammonium lactate, and wherein lactic acid is isolated by:

subjecting the fermentation liquid to an ultrafiltration step to result in a substantially polymer-free permeate containing ammonium lactate, subjecting the product of the ultrafiltration to ion exchange with a chelating resin to remove calcium and magnesium ions, subjecting the product of the ion exchange to a first electrodialysis using conventional electrodialysis membranes and a second electrodialysis using bipolar membranes to convert ammonium lactate into lactic acid and ammonium hydroxide, subjecting the lactic acid-containing product of the second dialysis to (1) ion exchange using a strong cationic ion exchanger and ion exchange using a weak anionic anionic ion exchanger or (2) a third electrodialysis step in which the pH of the lactic acid-containing solution is adjusted to a value in the range of about 1.5–2.5, and concentrating the result lactic acid to a desired concentration.

* * * * *